(12) United States Patent
Luebke et al.

(10) Patent No.: US 9,969,823 B1
(45) Date of Patent: *May 15, 2018

(54) SYNTHESIS AND POLYMERIZATION OF VINYL TRIAZOLIUM IONIC LIQUIDS

(71) Applicant: United States Department of Energy, Washington, DC (US)

(72) Inventors: David Luebke, Bethel Park, PA (US); Hunaid Nulwala, Pittsburgh, PA (US); Krzysztof Matyjaszewski, Pittsburgh, PA (US); Brian Adzima, San Francisco, CA (US)

(73) Assignee: The United States of America as represented by the Department of Energy, Washington, DC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/951,210

(22) Filed: Nov. 24, 2015

Related U.S. Application Data (63) Continuation-in-part of application No. 13/223,465, filed on Sep. 1, 2011, now Pat. No. 8,907,105.

(60) Provisional application No. 62/083,989, filed on Nov. 25, 2014.

(51) Int. Cl.
| | |
|---|---|
| *C08F 26/06* | (2006.01) |
| *C07D 249/04* | (2006.01) |
| *C07D 401/04* | (2006.01) |
| *C07D 249/06* | (2006.01) |

(52) U.S. Cl.
CPC ............ *C08F 26/06* (2013.01); *C07D 249/04* (2013.01); *C07D 249/06* (2013.01); *C07D 401/04* (2013.01)

(58) Field of Classification Search
CPC ....................................................... C08F 26/06
See application file for complete search history.

(56) References Cited

U.S. PATENT DOCUMENTS

2011/0236295 A1* 9/2011 Anderson et al. ......... 423/437.1

OTHER PUBLICATIONS

Krasovsky, 2003, Russian Chemical Bulletin, vol. 52, No. 8, p. 1791-1796.*

* cited by examiner

*Primary Examiner* — Rebecca L Anderson
*Assistant Examiner* — Karen Cheng
(74) *Attorney, Agent, or Firm* — Timothy L. Harney; Daniel D. Park; Brian J. Lally (57) ABSTRACT

Herein, we describe polymerized ionic liquids, demonstrate the synthesis of polymerized ionic liquids, and demonstrate the polymerization of triazolium monomers. One embodiment shows the polymeriazation of the triazolium monomers with bis(trifluoromethanesulfonyl)imide anions. In another embodiment we show the feasibility of copolymerizing with commodity monomers such as styrene using free radical polymerization techniques.

7 Claims, 4 Drawing Sheets

SYNTHESIS AND POLYMERIZATION OF VINYL TRIAZOLIUM IONIC LIQUIDS

RELATED APPLICATIONS

This application is a Continuation in Part of U.S. patent application Ser. No. 13/223,465 with a filing date of Sep. 1, 2011, now U.S. Pat. No. 8,907,105. This application also claims the benefit of U.S. provisional application 62/083,989 with a filing date of Nov. 25, 2014.

The entire disclosures of these related applications are expressly incorporated herein by reference.

GOVERNMENT INTEREST

The United States Government has rights in this invention pursuant to the employer-employee relationship between the Government and one or more of the inventors who are U.S. Department of Energy employees at the National Energy Technology Laboratory, Pittsburgh, Pa.

FIELD OF THE INVENTION

One or more embodiments consistent with the present disclosure relate to t monomers, methods of their preparation and methods for using the compounds described in various applications.

BACKGROUND

Ionic liquids (IL) are organic salts that are commonly liquid at room temperature. ILs have also been defined as molten salts having a melting point below 100° C. Recent interest in room temperature ionic liquids has increased due to unique characteristics of those compounds, such as a unique solubility, negligible vapor pressure, a wide electrochemical window and good thermal stability. Due to the negligible vapor pressure of ILs, they have been identified as environmentally friendly as they would not contribute to air pollution or to the generation of potentially toxic emissions when used as a solvent. As a result of these advantageous characteristics, ILs have potential use in a number of applications, including but not limited to synthesis, as both solvents and catalysts; energy storage, as electrolytes; extraction of radioactive materials, metals and organic liquids; polymer processing; cellulose processing; and gas separations.

The liquid nature of ionic liquids is a barrier for these materials to be used in many device based applications. Poly(ionic liquids)s (PILs) offer a unique combination of properties including, but not limited to, the ability to be processed in into films, cross-linked materials, vesicles, and gels, all while maintaining the highly desirable properties of ILs such as solubility, high conductivity, low vapor pressure and broad electrochemical and thermal stability. The unique combination of characteristics of PILs has led to interest in technologically important applications such as antimicrobial coatings, water purification, electrolytes for batteries, and gas separation membrane sensors, among others.

The most common strategy for preparing polymerizable ionic liquid (IL) monomers is to conjugate an IL moiety to a conventional polymerizable group, e.g. (meth)acrylate, styrene, or norborene, which allows the use of well-understood polymerization techniques. This approach does allow a variety of methyl and ethylene oxide spacer groups to be placed between the IL moiety and the polymer backbone, which reduces the PILs glass transition temperature (Tg), and increases the ionic conductivity. However, in many cases conjugation to large polymerizable moieties significantly reduces the functional diversity of pendant groups to simple alkyl chains, and decreases the concentration of IL groups in the resulting polymer. The decreased concentration of IL groups in the resulting polymer can be addressed by the polymerization of simpler vinyl functionalized ILs, such guanidinium, pyrrolidinium, and pyridinium cations; however, synthetic diversity in those cations is difficult to achieve. Functional imidazolium monomers are easily prepared from commercially available n-vinyl imidazole, and do allow variety of functional groups to be directly prepared via quaterization. However, while additional functionalization at the 2 and 5 positions of the ring is possible, most work has focused only on the 1,4-functionalized imidazolium cations, and only alkyl substitutions are commonly encountered. In addition, the vinyl bond on imidazolium is always on the 1 position of the imidazole ring resulting in difficult polymerization reaction.

SUMMARY

One or more embodiments consistent with the present disclosure generally relate to a novel class of 4-vinyl-1,2,3-triazolium monomers. These ionic monomers have improved properties over other classes of ionic monomers mainly its ability to polymerize itself and other commodity polymers such as styrenics and acrylates and methyl acrylate (Radically polymerized monomers). B. Adzima et al. J. Polym. Sci. Part A Polym. Chem. 2013, which is herein incorporated in its entirety.

Poly(triazoles) are highly versatile materials that can also be easily copolymerized with acrylates, methylacrylates, and styrenics. Functional triazole monomers can be easily prepared, and the synthesis of over 40 unique species has been reported with the ability to access targeted properties. K. Takizawa et al. J. Polym. Sci. Part A: Polym. Chem. 2008, 46, 5474, which is herein incorporated in its entirety. Also, specific regio-isomers of vinyl-triazoles have been reported by Nulwala et al. Macromolecules 2009, 42, 6068-6074, which is herein incorporated in its entirety. The versatile nature of the ring allows to also develop N-vinyl triazoles which has been reported by Nulwala et al. Macromolecules 2010, 43, 5474-5477. The 1-4-disubstituted 1,2,3-triazoles can be quaternized with a variety of side groups, allowing functionalization at three positions. H. B. Nulwala et al. Green Chem. 2011, 13, 3345, which is herein incorporated in its entirety.

The polymerized poly(triazoles) can also be converted in to ionic polymers due to its versatility using various post modification techniques resulting in a different method for accessing ionic polymers. However, post functionalization results in lower control over the molecular architecture.

BRIEF DESCRIPTION OF THE DRAWINGS

These and other features, aspects, and advantages of the multiple embodiments of the present invention will become better understood with reference to the following description, appended claims, and accompanied drawings where:

The details of some exemplary embodiments of the methods and systems of the present disclosure are set forth in the description below. Other features, objects, and advantages of the disclosure will be apparent to one of skill in the art upon examination of the following description, drawings, examples and embodiments. It is intended that all such additional systems, methods, features, and advantages be included within this description, be within the scope of the present disclosure.

DETAILED DESCRIPTION

Ionic liquids of one or more embodiments of the present invention relate to quaternary five-membered-ring heterocycles having three adjacent nitrogen atoms such as trisubstituted, 1,2,3,-triazolium salts with a polymerizable vinyl group side chain.

One or more embodiments of the present inventions relate to the synthesis and polymerization of functionalized vinyl 1,2,3-triazolium monomers.

The vinyl group on the triazolium ring can be homopolymerized. The obtained PIL can be used in variety of applications including gas separations.

The polymerizations can be performed with styrenics, methylacrylate, and acrylates. The copolymers can be used in variety of applications including gas separation.

Definitions

In describing the disclosed subject matter, the following terminology will be used in accordance with the definitions set forth below.

The term "heteroaryl" refers to an aryl group having one or more heteroatoms.

When referring to an alkane or alkene, the term "optionally substituted with at least one member selected from the group consisting of" means that one or more hydrogens on the carbon chain may be independently substituted with one or more of at least one member of the group. For example, substituted $C_2H_5$ may be, without limitations, $CF_2CF_3$, $CH_2CH_2OH$ or $CF_2CF_2I$.

The expression "$C_1$ to $C_n$ straight-chain, branched," where n is an integer defining the length of the carbon chain, is meant to indicate that $C_1$ and $C_2$ are straight-chain, and $C_3$ to $C_n$ may be straight-chain or branched.

The term "alkoxy" refers to a straight-chain or branched alkyl group bound via an oxygen atom and includes but is not limited to an alkoxy group bound to an alkane, alkene or aryl group, such as an ether group.

The term "styrene" refers to a class of organic compound monomers comprising the chemical formula $C_6H_5CH=CH_2$.

The term "styrenics" refers to a class of polymeric compounds derived from styrene.

The term "acrylate" refers to the salts, esters, and conjugate bases of acrylic acid as well as the derivatives of acrylic acid.

The term "methacrylate" refers to the salts and esters of methacrylic acid.

In one embodiment, the five-membered-ring heterocycle having three adjacent nitrogen atoms comprises a polymerized ionic liquid compound having the structure of Formula I:

where $R^1$, $R^2$ and $R^3$ each are independently selected from the group consisting of:
(i) H;
(ii) halogen;
(iii) $C_1$ to $C_{25}$ straight-chain, branched or cyclic alkane or alkene, optionally substituted with at least one member selected from the group consisting of Cl, Br, F, I, OH, $NH_2$ and SH;
(iv) $C_1$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{20}$ unsubstituted aryl, or $C_3$ to $C_{25}$ unsubstituted heteroaryl having one to three heteroatoms independently selected from the group consisting of O, N, Si and S; and,
(vi) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(1) $C_1$ to $C_{25}$ straight-chain, branched or cyclic alkane or alkene, optionally substituted with at least one member selected from the group consisting of Cl, Br, F I, OH, $NH_2$ and SH,
(2) OH,
(3) $NH_2$, and,
(4) SH;
(vii) At least one of the R groups on the triazolium ring is a radically polymerizable vinyl or alpha methyl group. and wherein $X^-$ is an anion.

The term "anion" refers to an ion having a negative charge. Preferably, anions include but are not limited to hydroxide, chloride, bromide, iodide, borate, tetrafluoroborate, cuprate, Cu(I)Cl$_2$ anion, phosphate, hexafluorophosphate, hexafluoroantimonate, perchlorate, bis[(trifluoromethyl)sulfonyl] amide, nitrite, nitrate, sulfate, a carboxylate, a sulfonate, a sulfonamide, a phosphonate, $PF_6$, $BF_4$, $NO_3$, halides, bis(trifluoromethylsulfonyl)imide, $(N(SO_2CF_3)_2$ or $Tf_2N)$, bis(methanesulfonyl)imide $(N(SO_2CH_3)_2)$, dictanimide (dca, $N(CN)_2$), alkylsulfate, alkylsulfonates, saccharinate, triflate $(SO_3CF_3)$, tosylate, acetate, lactate, tris(perfluoroalkyl)trifluorophosphate, trifluoroacetate, gluconate, ethylsulfate $(EtSO_4)$, tetrafluoroborate $(BF_4)$, docusate (doc), 2-(2-methoxy-ethoxy)-ethysulfate $(C_5H_{11}O_2SO_4)$, methylsulfate $(MeSO_4)$, acetate $(CH_3CO_2)$, trifluoroacetate $(CF_3CO_2)$, a mono- or diperfluorosulfonate, or any one of $(CF_3)_2PF_4$, $(CF_3)_3PF_3$, $(CF_3)_4PF_2$, $(CF_3)_5PF$, $(CF_3)_6P$, $SF_5CF_2SO_3$, $SF_5CHFCF_2SO_3$, $CF_3CF_2(CF_3)_2CO$, $(CF_3SO_2)_2CH$, $(SF_5)_3C$ and $(O(CF_3)_2C_2(CF_3)_2O)_2PO$ and amino acids including but not limited to glycine, histidine, glutamine, serine and leucine. A variety of anions can be used in the embodiments of the present invention giving purposeful results. Some of these anions include but are not limited to $BF_4$ and $PF_6$ being substituted for the $Tf_2N$. However, $Tf_2N$ based ILs will generally have lower $T_g$, higher $CO_2$ solubility and good thermal stability.

In additional embodiments, $R^1$, $R^2$ and $R^3$ are each independently selected from the group consisting of:
(i) halogen;
(ii) $C_1$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(iii) $C_3$ to $C_{25}$ unsubstituted heteroaryl having one to three heteroatoms independently selected from the group consisting of O, N, Si and S;
(iv) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(1) $C_1$ to $C_{25}$ straight-chain, branched or cyclic alkane or alkene, optionally substituted with at least one member selected from the group consisting of Cl, Br, F I, OH, $NH_2$ and SH,
(2) OH,
(3) $NH_2$, and,
(4) SH;
and wherein $X^-$ is an anion.

In one or more specific embodiments, $R^1$ $R^2$ or $R^3$ is a $C_2$ to $C_5$ alkene. Even more specifically, in one or more embodiments, $R^1$, $R^2$ or $R^3$ is a vinyl group.

In yet another embodiment, $R^1$ is a vinyl group.

In yet another embodiment, $R^3$ is a $C_2$ to $C_{10}$ straight chain alkane comprising one to three oxygen atoms. Even more preferably, $R^3$ is a $C_7$ straight chain alkane having three oxygen atoms.

In yet another embodiment, $R^1$ is a vinyl group, $R^3$ is an alkoxy group, $R^2$ is a $C_1$ to $C_{10}$ alkane and $X^-$ is selected from the group consisting of iodide, bromide, chloride, acetate and $Tf_2N$.

In another embodiment, $R^3$ is a $C_2$ to $C_5$ alkene and even more preferably $R^3$ is a vinyl group.

In yet another embodiment, $R^3$ is a $C_2$ to $C_5$ alkene and $R^1$ is an unsubstituted aryl, and even more preferably $R^3$ is a vinyl group and $R^1$ is a phenyl group.

In yet another embodiment, $R^1$ is a protected amino group.

In yet another embodiment, $R^1$ is a $C_1$ to $C_{25}$ straight-chain, branched or cyclic alkane substituted with at least one —$NH_2$ group and $R^3$ is $C_2$ to $C_{10}$ straight chain alkane comprising one to three oxygen atoms. Even more preferably, $R^3$ is a $C_7$ straight chain-alkane having three oxygen atoms.

In yet another embodiment, $R^3$ is a $C_6$ to $C_{25}$ substituted heteroaryl having one to three nitrogen atoms. Even more preferably, $R^3$ is a $C_5$ substituted heteroaryl having 1 nitrogen atom, also known as pyridine.

In yet another embodiment, $R^3$ is a $C_6$ to $C_{25}$ substituted heteroaryl having one to three nitrogen atoms and $R^1$ is a $C_6$ to $C_{25}$ unsubstituted aryl group. Even more preferably, $R^3$ is a pyridine and $R^1$ is a phenyl group.

In yet another embodiment, $R^1$ is a $C_1$ to $C_{25}$ straight-chain or branched alkane comprising one to three silicon atoms. Even more preferably, $R^1$ is a silyl group having three methyl groups, commonly referred to as a trimethylsilyl group.

In yet another embodiment, $R^1$ is a $C_1$ to $C_{25}$ straight-chain or branched alkane comprising one to three silicon atoms and $R^3$ is either a $C_1$ to $C_{12}$ straight-chain or branched alkane or a $C_5$ to $C_{10}$ unsubstituted aryl group. Even more preferably, $R^1$ is a silyl and $R^3$ is a phenyl or alkyl group.

In yet another embodiment, $R^3$ is a $C_1$ to $C_{25}$ straight-chain or branched alkane comprising one to three silicon atoms. Even more preferably, $R^3$ is a silyl group having three methyl groups.

In yet another embodiment, $R^3$ is a $C_1$ to $C_{25}$ straight-chain or branched alkane comprising one to three silicon atoms and $R^1$ is a $C_1$ to $C_{12}$ straight-chain or branched alkane or a $C_5$ to $C_{10}$ unsubstituted aryl group.

In another embodiment, $R^3$ is a $C_1$ to $C_{25}$ straight-chain, branched or cyclic alkane or alkene substituted with at least one fluorine atom.

In yet another embodiment, $R^3$ is a $C_1$ to $C_{25}$ straight-chain, branched or cyclic alkane or alkene substituted with at least one fluorine atom and $R^1$ is a $C_5$ to $C_{10}$ unsubstituted aryl group.

In another embodiment, $R^1$ is a $C_2$ to $C_{10}$ straight chain alkane comprising one to three oxygen atoms. Even more preferably $R^1$ is a $C_7$ straight-chain alkane comprising three oxygen atoms.

In yet another embodiment, $R^1$ is a $C_2$ to $C_{10}$ straight chain alkane comprising one to three oxygen atoms and $R^3$ is a $C_6$ to $C_{25}$ substituted heteroaryl having one to three nitrogen atoms. More preferably, $R^1$ is a $C_7$ straight chain alkoxy having three oxygen atoms and $R^3$ is a pyridine group.

The multiple embodiments will be further described with reference to the following Examples. However, the examples below are to be construed as merely illustrative, and not limiting of the remainder of the disclosure in any way whatsoever. Without further elaboration, it is believed that one skilled in the art can, based on the description herein, utilize the present disclosure to its fullest extent and perform the methods and systems disclosed herein. All publications recited herein are hereby incorporated by reference in their entirety.

General Synthesis of Tri-Substituted 1,2,3-Triazolium Ionic Liquids

The present example demonstrates general methods that may be used in the synthesis of the triazolium-based ionic compounds of the present invention. However, many other reagents and modification to the steps described below may also be used in accordance with the multiple embodiments of the present invention.

General Reaction to Form Triazolium-Based ILs

The general procedure for the preparation of 1,2,3-triazolium ILs follows the reaction outlined in Equation 1.

Equation 1

More specifically, alkyne, azide CuSO$_4$ and sodium ascorbate are added to an aqueous medium. The resulting triazole can subsequently be refluxed with excess X—R$^3$.

However, one embodiment of the present invention can be used as a one-step synthetic route to vinyl triazoles from commercially available vinyl acetylene. This embodiment results in an optimized synthesis, eliminating the need for any secondary reactions and purifications. The general procedure for the one-step synthesis of functionalized vinyl triazoles can be seen in Equation 2.

Equation 2

In a 100 ml schlenk flask 10 g of azide and 0.02 molar equivalents of Cu (3% wt. Cu/C) were combined with 16-26 g of tetrahydrofuran (THF). The mixture was then frozen using liquid nitrogen and the flask evacuated to less than 1 mm Hg pressure. Afterwards, 1.1 molar equivalents of vinyl acetylene and triethylamine were then transferred via syringe and condensed in the flask. The mixture was then allowed to warm to room temperature, before being immersed in a 50° C. bath. The reaction was then monitored using FTIR spectroscopy. Many of the reactions were complete in 2 to 4 hours, but most were allowed to proceed overnight. Afterwards the Cu/C was filtered off and washed with dichloromethane, methanol, and acetone. The mixed solvents were then evaporated and the product dissolved in dichloromethane. The mixture was then washed with 0.5 M EDTA, and the solvent evaporated.

The triazole was dissolved in methyl iodide (approximately 2.0 molar equivalents were required to maintain a viscosity suitable for magnetic stirring) and allowed to react at room temperature for 2-3 days. The reaction could be accelerated by refluxing at 39° C., although evaporation of the methyl iodide was problematic over longer time scales. Afterwards the remaining methyl iodide was evaporated. The iodide salts were readily soluble in water or methanol and any remaining triazole or other organic impurity could be removed by washing with ethyl acetate (or hexanes if dissolved in methanol).

In one embodiment, metathesis was performed with lithium bis(trifluoromethanesulfonyl)amide, 1.1 equivalents of lithium bis(trifluoromethanesulfonyl)amide were added in water (66% Li-Tf$_2$N by weight) to an aqueous solution of the triazolium iodide. Phase separation allowed to occur and took place in as little as a minute. The ionic liquids could then be recovered by extraction with diethyl ether or ethyl acetate.

For the polymerizations in solvents, a mixture comprising monomer, initiator (0.005 molar equivalents to monomer), and dimethylformamide (50% by weight) was prepared and then subjected to three freeze-pump-thaw cycles. For the neat ionic liquid polymerizations a vacuum was pulled on the mixture in the liquid state until the pressure dropped below 200 mTorr. The reaction vessel was then heated at 70° C. and samples were periodically withdrawn under argon using a syringe. Conversion was determined via 1H NMR.

Afterwards the polymers were dissolved in THF (approximately 30% weight polymer), and then precipitated into water (TEGTz Tf$_2$N and EtOHTz Tf$_2$N), 20/80 water and methanol (DTz Tf$_2$N), or diethyl ether (all others). Removal of the DMF prior to precipitation using the vacuum line increased the yield.

The resulting ILs were typically soluble in a wide range of organic solvents varying in polarity from methanol to dichloromethane (see Supporting Information). TEGTz Tf$_2$N and EtOHTz Tf$_2$N were soluble in water. Most of the ILs were amorphous in nature showing no melting transition by DSC. However, the pyridinium functionalized IL (PTz Tf$_2$N) immediately crystallized (melting temperature: 67±2° C.) and the benzyl functionalized IL (BTz Tf$_2$N) was found to crystallize after storage at 0° C. for over 1 month (melting temperature, 19° C.). In all cases, the Tg were far below room temperature. The lowest Tg was found in the Hexyl functionalized species (HTz Tf$_2$N), and the highest in the BOC protected amine (BOCNEtTz Tf$_2$N). In literature, typically, lower Tg values correlate well with increased ionic and electrical conductivity.

Figure 1:
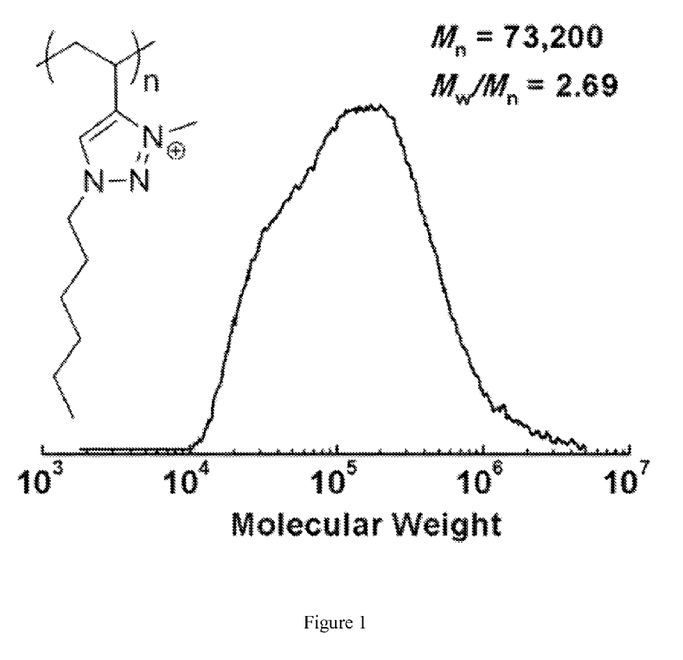
FIG. 1 is the gel permeation chromatography (GPC) graph for the polymerized ionic liquids with polystyrene standards.
Figure 2:
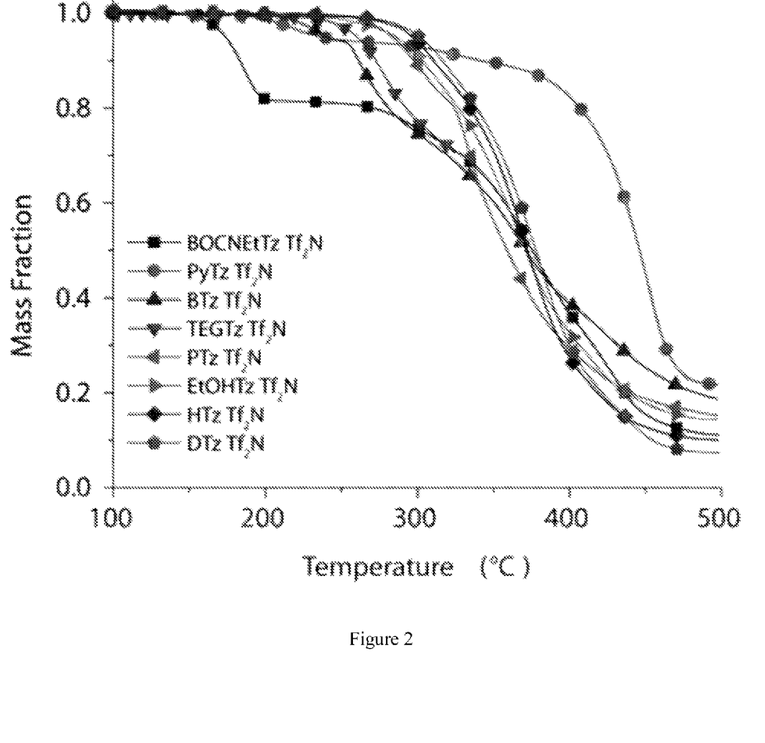
FIG. 2 is a graphical representation of the thermal decomposition temperature of various embodiments with $Tf_2N$ as the anion.

Neat IL monomers readily polymerized at 70° C. using azobisisobutyronitrile (AIBN) as an initiator (Table 1). Simply pulling a vacuum on the mixture allowed facile degasing without the need for freeze-pump-thaw cycles due to the negligible vapor pressure of the IL monomers and low oxygen solubility. The solid PyTz Tf$_2$N and the extremely viscous BOCNEtTz Tf$_2$N were polymerized in 50% wt DMF. Conversion was determined by 1H NMR using the 5-H proton on the triazolium ring (or the solvent peak) as the internal standard. In most cases, the monomer conversion was >70% after 24 h. Due to the ionic nature of the PILs, the molecular weight could not be verified by conventional size exclusion chromatography; however, in a solvent containing 10 mM LiTf$_2$N and 10 mM 1-butylimidazole, molecular weight values in the range of 73-434 kDa were observed (relative to the calibration standard of poly(1-(4-vinylbenzyl)-3-butyl imidazolium bis(trifluoromethanesulfonyl)imide. The molecular weight distribution was found to be highly dependent on the type of pendent group (ranging from 1.8 to 7.10) depending on the PIL. This wide range in molecular weight and molecular weight distribution including bimodal peaks may arise as the different side groups would interact differently with the anion. This may be one possible explanation of nonsymmetrical peaks seen in GPC. Typical GPC curve for these PIL is shown in FIG. 1.

Random copolymerization of BTz Tf$_2$N with styrene was also performed. Mixtures consisting of 0.66:1.00 BTz Tf$_2$N to styrene readily underwent free radical polymerization in DMF. 1H NMR confirmed complete conversion of both styrene and DTz, while GPC showed a single peak, similar to those for the homo PILs. These results suggest that copolymerization of vinyl-triazolium Tf$_2$N monomers with commodity monomers is feasible.

All of the polymers except p(BTz Tf$_2$N) showed consistent solubility in aprotic solvents ranging in polarity from dimethylsulfoxide to ethyl acetate. However, solubility in other solvents was dictated by the pendant functional groups. The p(HTz Tf$_2$N) and p(DTz Tf$_2$N) were soluble in hexanes due to their pendant alkyl chains, while p(EtOHTz Tf$_2$N), p(TEGTz Tf$_2$N), and p(BOCNEtTz Tf$_2$N) were all soluble in methanol. None of the polymers dissolved in water due to the Tf$_2$N anion (Table 3).

Figure 3:
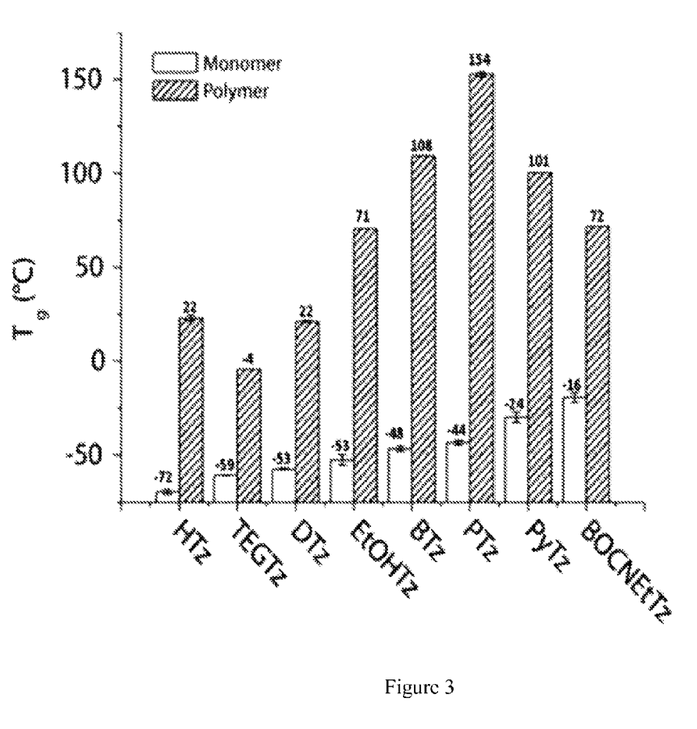
FIG. 3 shows the change in glass transition temperature of between the monomeric triazoliums vs. poly(triazolium) ionic liquids

The thermal stability of PILs has been shown to be dictated by the anion and halides show considerably lower thermal decomposition temperatures than large bulky anions such as Tf$_2$N, BF$_4$, and PF$_6$. The effect of pendant functional groups has not been well addressed. Here, it is evident that pendant functional groups play a key role (FIG. 3). The p(PyTz Tf$_2$N), p(BTz Tf$_2$N), and p(TEGTz Tf$_2$N) show considerable low mass losses of 5% (FIG. 3). The remaining PILs bearing phenyl, ethanol, hexyl, and decyl groups show 5% mass losses that are comparable to poly(imidazolium Tf$_2$N) polymers with similar functional groups of around 300° C. The p(BOCNEtTz Tf$_2$N) shows a 19% mass loss at ~175° C., corresponding to the loss of the BOC protecting group. The free amine functionalized polymer then showed stability comparable to the more stable PILs.

DSC showed that the glass transition temperatures were elevated by 71-154° C. relative to the monomers, and that pendant group variation produced a wide range of T$_g$ (FIG. 3). The largest increase was seen in the p(PTz Tf$_2$N), perhaps due to p-p stacking of the phenyl groups. Similarly, the aromatic p(PyTz Tf$_2$N) and p(BTz Tf$_2$N) showed large increases. The lowest Tg's were observed in the alkyl and TEG functional groups. The p(TEGTz Tf$_2$N) had a T$_g$ below ambient (24° C.) and was a very viscous liquid at room temperature. The p(DTz Tf$_2$N) and p(HTz Tf$_2$N) also showed ambient T$_g$ values, but were solids.

Figure 4:
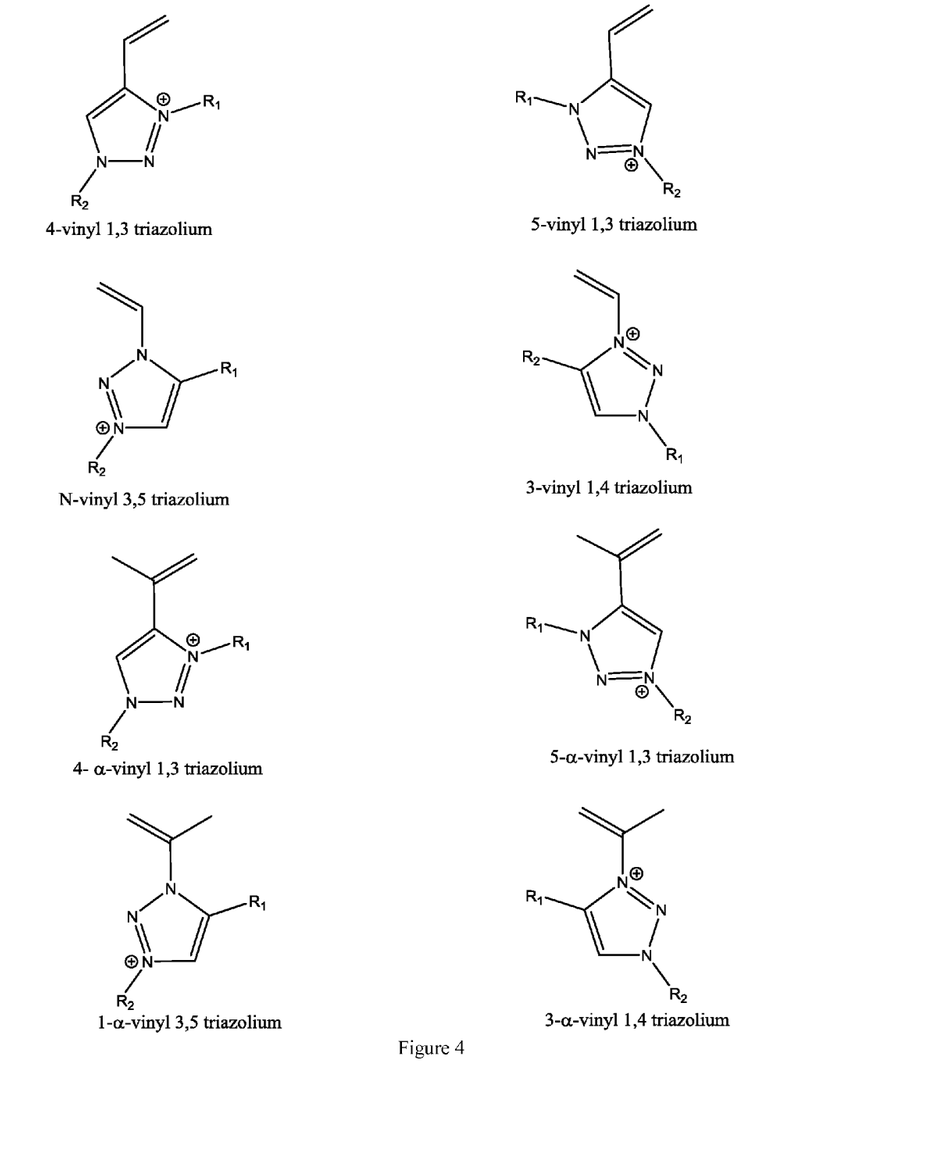
FIG. 4 shows various vinyl triazolium isomeric monomers which can be accessed with 2+3 cycloaddition reactions.

Copolymerization of 1-Functionalized-3-Methyl-4-Vinyl 1,2,3-Triazolium Monomer and Styrene In an ampule of styrene, 1-Functionalized-3-Methyl-4-Vinyl 1,2,3-triazolium monomer (DVt Tf$_2$N) (0.66 molar eq.), and AIBN (0.016 molar equivalents to styrene) were combined. DMF was then added such that the mixture was 50% solvent by weight, and the vessel then subjected to three freeze-pump-thaw cycles. The reaction vessel was then heated for 24 hours at 70° C. After incubation, the DMF was evaporated. The resulting polymer was redissolved in THF, and precipitated in diethyl ether. FIG. 4 shows various vinyl triazolium isomeric monomers which can be accessed through 2+3 cycloaddition reactions.

In addition to styrene, DVt Tf2N monomers can be copolymerized by polystyrenes, acrylates and methacrylates as defined in the previous "definitions" section.

Some examples of the copolymerized ionic liquids are: 1-Benzyl-3-methyl-4-vinyl-triazolium bis(trifluoromethanesulfonyl)amide, 1-Hexyl-3-methyl-4-vinyl-triazolium bis(trifluoromethanesulfonyl)amide, 1-decyl-3-methyl-4-vinyl-triazolium bis(trifluoromethanesulfonyl)amide, 2-(3-methyl-4-vinyl-triazolium-1-yl)ethanol bis(trifluoromethanesulfonyl)amide, Tert-butyl N-[2-(4-vinyltriazol-1-yl) ethyl]carbamates, 1-phenyl-3-methyl-4-vinyl-triazolium bis (trifluoromethanesulfonyl)amide, 1-(1-pyridine)-3-methyl-4-vinyl-triazolium bis(trifluoromethanesulfonyl)amide, and 1-TEG-3-methyl-4-vinyl-triazolium bis(trifluoromethanesulfonyl)amide.

Example 1

Preparation of 1-Benzyl-3-methyl-4-vinyl-triazolium bis(trifluoromethansulfonyl)amide In an ampule of styrene, 1-Benzyl-3-methyl-4-vinyl-triazolium bis(trifluoromethansulfonyl)amide (BTz Tf$_2$N) (0.66 molar eq.), and AIBN (0.016 molar equivalents to styrene) were combined. DMF was then added such that the mixture was 50% solvent by weight, and the vessel then subjected to three freeze-pump-thaw cycles. The reaction vessel was then heated for 24 hours at 70° C. After incubation, the DMF was evaporated. The resulting polymer was redissolved in THF, and precipitated in diethyl ether. The following structure was confirmed:

Yield: 93%. 1H NMR (500 MHz, DMSO-d6, δ): 9.26 (s, 1H), 7.75-7.24 (m, 5H), 6.89 (dd, J=11.4, 17.6, 1H), 6.28 (d, J=17.6, 1H), 5.95 (d, J=11.4, 1H), 5.86 (t, 2H), 4.27 (s, 3H). 13C NMR (126 MHz, CDCl3, d): 146.5, 138.0, 134.3, 61.5, 43.0. Mass Spec: calculated for C$_{14}$H$_{14}$F$_6$N$_4$O$_4$S$_2$ 480.04: observed, 479.97 (Da).

Example 2

Preparation of 1-Hexyl-3-methyl-4-vinyl-triazolium bis(trifluoromethansulfonyl)amide In an ampule of styrene, 1-Hexyl-3-methyl-4-vinyl-triazolium bis(trifluoromethansulfonyl)amide (HTz Tf$_2$N) (0.66 molar eq.), and AIBN (0.016 molar equivalents to styrene) were combined. DMF was then added such that the mixture was 50% solvent by weight, and the vessel then subjected to three freeze-pump-thaw cycles. The reaction vessel was then heated for 24 hours at 70° C. After incubation, the DMF was evaporated. The resulting polymer was redissolved in THF, and precipitated in diethyl ether. The following structure was confirmed:

Yield: 90%. 1H NMR (500 MHz, DMSO-d6, d): 9.21 (s, 1H), 6.91 (dd, J=11.4, 17.6, 1H), 6.24 (d, J=17.5, 1H), 5.97 (d, J=11.5, 1H), 4.58 (t, J=7.2, 2H), 4.27 (s, 3H), 1.99-1.86 (m, 2H), 1.30 (s, 6H), 0.88 (t, J=6.9, 3H). 13C NMR (126 MHz, CDCl3, d): 146.1, 131.6, 124.2, 58.4, 35.7, 33.6, 30.25, 19.0, 5.25. Mass Spec: calculated for C$_{13}$H$_{20}$F$_6$N$_4$O$_4$S$_2$, 474.08: observed, 473.97 (Da).

Example 3

Preparation of 1-Decyl-3-methyl-4-vinyl-triazolium bis(trifluoromethansulfonyl)amide In an ampule of styrene, 1-Decyl-3-methyl-4-vinyl-triazolium bis(trifluoromethansulfonyl)amide (DTz Tf$_2$N) (0.66 molar eq.), and AIBN (0.016 molar equivalents to styrene) were combined. DMF was then added such that the mixture was 50% solvent by weight, and the vessel then subjected to three freeze-pump-thaw cycles. The reaction vessel was then heated for 24 hours at 70° C. After incubation, the DMF was evaporated. The resulting polymer was redissolved in THF, and precipitated in diethyl ether. The following structure was confirmed:

Yield: 87% for quaterization and metathesis. 1H NMR (500 MHz, DMSO-d6, d): 9.18 (s, 1H), 6.89 (dd, J=11.5, 17.5, 1H), 6.09 (dd, J=14.5, 139.8, 2H), 4.56 (t, J=7.1, 2H), 4.25 (s, 3H), 1.92 (m, 2H), 1.28 (m, 14H), 0.85 (d, J=7.0, 3H). 13C NMR (126 MHz, CDCl3, d): 146.1, 131.6, 124.2, 58.4, 42.9, 36.5, 34.1, 34.0, 33.9, 33.7, 33.5, 30.6, 27.3, 19.12, 5.3. Mass Spec: calculated for $C_{17}H_{28}F_6N_4O_4S_2$, 530.15: observed, 530.02 (Da).

Example 4

Preparation of 2-(3-Methyl-4vinyl-triazolium-1-yl)ethanol bis(trifluoromethansulfonyl)amide In an ampule of styrene, 2-(3-Methyl-4vinyl-triazolium-1-yl)ethanol bis(trifluoromethansulfonyl)amide (EtOHTz Tf$_2$N) (0.66 molar eq.), and AIBN (0.016 molar equivalents to styrene) were combined. DMF was then added such that the mixture was 50% solvent by weight, and the vessel then subjected to three freeze-pump-thaw cycles. The reaction vessel was then heated for 24 hours at 70° C. After incubation, the DMF was evaporated. The resulting polymer was redissolved in THF, and precipitated in diethyl ether. The following structure was confirmed:

Yield: 82%. 1H NMR (500 MHz, DMSO-d6, d): 9.19 (s, 1H), 6.91 (dd, J=11.5, 17.6, 1H), 6.28 (d, J=17.6, 1H), 5.96 (d, J=11.5, 1H), 5.39-5.05 (m, 1H), 4.70-4.57 (m, 2H), 4.28 (d, J=3.7, 3H), 3.98-3.79 (m, 2H). 13C NMR (126 MHz, CDCl3, d): 145.9, 131.6, 126.0, 124.1, 123.4, 64.0, 61.4, 42.8. Mass Spec: calculated for $C_9H_{12}F_6N_4O_5S_2$, 434.02: observed, 434.52 (Da).

Example 5

Preparation of Tert-butyl N-[2-(4-vinyltriazol-1-yl) ethyl]carbamates

In an ampule of styrene, Tert-butyl N-[2-(4-vinyltriazol-1-yl)ethyl]carbamates (BOCNEtTz Tf$_2$N) (0.66 molar eq.), and AIBN (0.016 molar equivalents to styrene) were combined. DMF was then added such that the mixture was 50% solvent by weight, and the vessel then subjected to three freeze-pump-thaw cycles. The reaction vessel was then heated for 24 hours at 70° C. After incubation, the DMF was evaporated. The resulting polymer was redissolved in THF, and precipitated in diethyl ether. The following structure was confirmed:

Yield: 51%. 1H NMR (500 MHz, DMSO-d6, d): 8.13 (s, 1H), 6.69 (dd, J=11.2, 17.7, 1H), 5.81 (dd, J=1.5, 17.8, 1H), 5.27 (dd, J=1.6, 11.2, 1H), 4.36 (t, J=6.1, 2H), 3.36 (dd, J=6.0, 12.1, 2H), 1.34 (s, 9H). 13C NMR (126 MHz, CDCl3, d): 160.9, 146.0, 131.7, 124.0, 83.61, 58.97, 45.3, 44.5, 33.3, 12.6, 5.3. Mass Spec: calculated for $C_{29}H_{49}F_6N_8O_6S_2$, 533.08: observed, 533.07 (Da).

Example 6

Preparation of 1-Phenyl-3-methyl-4-vinyl-triazolium bis(trifluoromethansulfonyl)amide In an ampule of styrene, 1-Phenyl-3-methyl-4-vinyl-triazolium bis(trifluoromethansulfonyl)amide (PTz Tf$_2$N) (0.66 molar eq.), and AIBN (0.016 molar equivalents to styrene) were combined. DMF was then added such that the mixture was 50% solvent by weight, and the vessel then subjected to three freeze-pump-thaw cycles. The reaction vessel was then heated for 24 hours at 70° C. After incubation, the DMF was evaporated. The resulting polymer was redissolved in THF, and precipitated in diethyl ether. The following structure was confirmed:

Yield: 93%. 1H NMR (500 MHz, DMSO-d6, d): 9.86 (s, 1H), 8.09-7.67 (m, 5H), 7.00 (dd, J=11.5, 17.6, 1H), 6.34 (d, J=17.5, 1H), 6.05 (d, J=11.5, 1H), 4.40 (s, 3H), 3.32 (s, 2H). ESI1: 186.10 (calc.), 185.95 (found). 13C NMR (126 MHz, CDCl3, d): 147, 140.0, 135.6, 131.2, 126.6, 124.11, 123.43, 43.32, 5.3. Mass Spec: calculated for $C_{13}H_{12}F_6N_4O_4S_2$: 466.02; observed, 466.03 (Da).

Example 7

Preparation of 1-(1-Pyridine)-3-methyl-4-vinyl-triazolium bis(trifluoromethansulfonyl)amide In an ampule of styrene, 1-(1-Pyridine)-3-methyl-4-vinyl-triazolium bis(trifluoromethansulfonyl)amide (PyTz Tf$_2$N) (0.66 molar eq.), and AIBN (0.016 molar equivalents to styrene) were combined. DMF was then added such that the mixture was 50% solvent by weight, and the vessel then subjected to three freeze-pump-thaw cycles. The reaction vessel was then heated for 24 hours at 70° C. After incubation, the DMF was evaporated. The resulting polymer was redissolved in THF, and precipitated in diethyl ether. The following structure was confirmed:

Yield: 90%. 1H NMR (500 MHz, DMSO-d6, d): 9.51 (s, 1H), 9.17 (d, 2H), 8.64 (d, 2H), 6.85 (dd, 1H), 6.08 (d, 1H), 5.56 (d, 1HH), 4.36, (s, 1H) 13C NMR (126 MHz, CDCl3, d): 153.1, 152.5, 152.1, 129.9, 123.7, 121.7, 121.5, 63.15, 52.7, 5.3. Mass Spec: calculated for $C_{12}H_{11}F_6N_5O_4S_2$, 467.02: observed, 467.01 (Da).

Example 8

Preparation of 1-TEG-3-methyl-4-vinyl-triazolium bis(trifluoromethansulfonyl)amide In an ampule of styrene, 1-TEG-3-methyl-4-vinyl-triazolium bis(trifluoromethansulfonyl)amide (TEGTz $Tf_2N$) (0.66 molar eq.), and AIBN (0.016 molar equivalents to styrene) were combined. DMF was then added such that the mixture was 50% solvent by weight, and the vessel then subjected to three freeze-pump-thaw cycles. The reaction vessel was then heated for 24 hours at 70° C. After incubation, the DMF was evaporated. The resulting polymer was redissolved in THF, and precipitated in diethyl ether. The following structure was confirmed:

Yield: 75%. 1H NMR (500 MHz, DMSO-d6) d 5 9.15 (s, 1H), 6.91 (dd, 1H), 6.27 (d, 1H), 5.98 (d, 1H), 4.79 (t, 2H), 4.30 (s, 3H), 3.6-3.58 (m, 2H), 3.52-3.47 (m, 4H), 3.42-3.40 (m, 2H), 3.23 (s, 3H.) 13C NMR (126 MHz, CDCl3, d): 146.0, 131.7, 124.1, 76.47, 74.8, 72.4, 63.3, 58.5, 42.3, 5.3. Mass Spec: calculated for $C_{14}H_{22}F_6N_4O_7S_2$, 536.08: observed, 536.11 (Da).

It is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

It should be noted that ratios, concentrations, amounts, and other numerical data may be expressed herein in a range format or as an approximation. It is to be understood that such a range or approximation is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include .+−.1%, .+−.2%, .+−.3%, .+−.4%, .+−.5%, .+−.6%, .+−.7%, .+−.8%, .+−.9%, or .+−.10%, or more of the numerical value(s) being modified.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

TABLE 1

| Monomer | Conv. (%) | Solvent |
|---|---|---|
| EtOHTz Tf$_2$N | 60 | — |
| PyTz Tf$_2$N | 69 | 50% DMF |
| HTz Tf$_2$N | 88 | — |
| BOCNEtTz Tf$_2$N | 70 | 50% DMF |
| TEGTz Tf$_2$N | 75 | — |
| PTz Tf$_2$N | 100 | — |
| DTz Tf$_2$N | 84 | — |
| BTz Tf$_2$N | 95 | — |

TABLE 2

| Monomer | [Inhibitor] (M) | $k_p/k_t^{0.5}$ |
|---|---|---|
| BOCNEtTz | 0.0030 ± 0.0014 | 1.4 ± 0.2 |
| BTz | 0.0040 ± 0.0008 | 2.8 ± 0.2 |
| HTz | 0.0126 ± 0.0026 | — |
| DTz | 0.0042 ± 0.0072 | 5.6 ± 2.1 |
| EtOHTz | 0.0108 ± 0.0058 | 8.2 ± 1.9 |

TABLE 3

| | Solubility (IL/PIL) (10 mg/ml) | | | | | | | |
|---|---|---|---|---|---|---|---|---|
| | H$_2$O | DMSO | DMF | ACN | MeOH | Acetone | Ethyl acetate | DCM | Hexanes |
| BMVT Tf$_2$N | −/− | +/− | +/+ | +/− | +/− | +/+ | +/+ | +/+ | −/− |
| EtOHMVT | +/− | +/+ | +/+ | +/+ | +/+ | +/+ | +/+ | +/− | −/− |
| PMVT Tf$_2$N | −/− | +/+ | +/+ | +/+ | +/− | +/+ | +/+ | +/+ | −/− |
| HMVT | −/− | +/+ | +/+ | +/+ | +/− | +/+ | +/+ | +/+ | −/+ |
| DMVT | −/− | +/+ | +/+ | +/+ | +/− | +/+ | +/+ | −/+ | −/+ |
| BOCEtAM | −/− | +/+ | +/+ | +/+ | +/+ | +/+ | +/+ | +/+ | −/− |
| TEGMVT | +/− | +/+ | +/+ | +/+ | +/+ | +/+ | +/+ | +/+ | −/− |

We claim:

1. A polymerized ionic liquid composition comprising 1-Benzyl-3-methyl-4-vinyl-triazolium bis(trifluoromethanesulfonyl)amide, 1-Hexyl-3-methyl-4-vinyl-triazolium bis(trifluoromethanesulfonyl)amide, 1-decyl-3-methyl-4-vinyl-triazolium bis(trifluoromethanesulfonyl)amide, 2-(3-methyl-4-vinyl-triazolium-1-yl)ethanol bis(trifluoromethanesulfonyl)amide, Tert-butyl N-[2-(4-vinyltriazol-1-yl)ethyl]carbamate, 1-phenyl-3-methyl-4-vinyl-triazolium bis(trifluoromethanesulfonyl)amide, 1-(1-pyridine)-3-methyl-4-vinyl-triazolium bis(trifluoromethanesulfonyl)amide, and 1-TEG-3-methyl-4-vinyl-triazolium bis(trifluoromethanesulfonyl)amide.

2. The polymerized ionic liquid composition of claim 1, wherein polymerization can be carried out using a mixture comprising at least one monomer and at least one initiator to yield at least one polymerized ionic liquid.

3. The polymerized ionic liquid composition of claim 2, wherein polymerization can be carried out using a mixture comprising at least one monomer, at least one initiator, and at least one solvent to yield at least one polymerized ionic liquid.

4. The polymerized ionic liquid composition of claim 3, wherein said at least one solvent is selected from the group comprising: acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol dimethyl ether), 1,2-dimethoxy-ethane (glyme, DME), dimethylformamide (DMF), dimethyl sulfoxide (DMSO), 1,4-dioxane, ethanol, ethyl acetate, ethylene glycol, glycerin, heptane, Hexamethylphosphoramide (HMPA), Hexamethylphosphoroustriamide (HMPT), hexane, methanol methyl t-butylether (MTBE), methylene chloride (CH$_2$Cl$_2$), N-methyl-2-pyrrolidinone (NMP), nitromethane (CH$_3$NO$_2$), Petroleum ether (ligroine), 1-propanol, 2-propanol, pyridine, tetrahydrofuran (THF), toluene, triethylamine, water, o-xylene, m-xylene, p-xylene.

5. The polymerized ionic liquid composition of claim 2, wherein said initiator is a radical initiator.

6. The polymerized ionic liquid composition of claim 5, wherein said radical initiator is selected from the group of azo-initiators, inorganic initiators, ultraviolet light initiators, and organic peroxides.

7. The polymerized ionic liquid composition of claim 6, wherein:
   a. said azo-initiator is selected from the group consisting of: 4,4'-Azobis(4-cyanovaleric acid), 4,4'-Azobis(4-cyanovaleric acid), 1,1'-Azobis(cyclohexanecarbonitrile), 2,2'-Azobis(2-methylpropionamidine) dihydrochloride granular, 2,2'-Azobis(2-methylpropionitrile), 2,2'-Azobis(2-methylpropionitrile);

b. said inorganic initiator is selected from the group consisting of: Sodium persulfate, Potassium persulfate, Hydroxymethanesulfinic acid monosodium salt dehydrate, Ammonium persulfate; and c. said organic peroxide is selected from the group consisting of: tert-Butyl hydroperoxide, di-tert-butyl peroxide, tert-Butyl peracetate, cumene hydroperoxide, 2,5-Di(tert-butylperoxy)-2,5-dimethyl-3-hexyne, 2,5-Di(tert-butylperoxy)-2,5-dimethyl-3-hexyne, Dicumyl peroxide, 2,5-Bis(tert-butylperoxy)-2,5-dimethylhexane, 2,5-Bis(tert-butylperoxy)-2,5-dimethylhexane, 1,1-Bis(tert-butylperoxy)-3,3,5-trimethylcyclohexane, 1,1-Bis(tert-butylperoxy)cyclohexane, 1,1-Bis(tert-amylperoxy)cyclohexane, Benzoyl peroxide, 2-Butanone peroxide, Lauroyl peroxide, tert-Butyl peroxybenzoate, tert-Butylperoxy 2-ethylhexyl carbonate; and d. said ultraviolet light initiator is selected from the group consisting of: Acetophenone, Anisoin, Anthraquinone, Anthraquinone-2-sulfonic acid, sodium salt monohydrate, (Benzene) tricarbonylchromium, Benzil, Benzoin, Benzoin ethyl ether, 2 Benzoin isobutyl ether, Benzoin methyl ether, Benzophenone, Benzophenone/1-Hydroxycyclohexyl phenyl ketone, (Various blends), 3,3',4,4'-Benzophenonetetracarboxylic dianhydride, 4-Benzoylbiphenyl, 2-Benzyl-2-(dimethylamino)-4'-morpholinobutyrophenone, 4,4'-Bis(diethylamino)benzophenone, 4,4'-Bis(dimethylamino)benzophenone, Camphorquinone, 2-Chlorothioxanthen-9-one, (Cumene)cyclopentadienyliron(II) hexafluorophosphate, Dibenzosuberenone, 2,2-Diethoxyacetophenone, 4,4'-Dihydroxybenzophenone, 2,2-Dimethoxy-2-phenylacetophenone, 4-(Dimethylamino)benzophenone, 4,4'-Dimethylbenzil, 2,5-Dimethylbenzophenone, 3,4-Dimethylbenzophenone, Diphenyl(2,4,6-trimethylbenzoyl)phosphine oxide/2-Hydroxy-2-methylpropiophenone, (blends) 4'-Ethoxyacetophenone, 2-Ethylanthraquinone, Ferrocene, 3'-Hydroxyacetophenone, 4'-Hydroxyacetophenone, 3-Hydroxybenzophenone, 4-Hydroxybenzophenone, 1-Hydroxycyclohexyl phenyl ketone, 2-Hydroxy-2-methylpropiophenone, 2-Methylbenzophenone, 3-Methylbenzophenone, Methybenzoylformate, 2-Methyl-4'-(methylthio)-2-morpholinopropiophenone, Phenanthrenequinone, 4'-Phenoxyacetophenone, Thioxanthen-9-one, Triarylsulfonium hexafluoroantimonate mixed in propylene carbonate, Triarylsulfonium hexafluorophosphate salts mixed in propylene carbonate.

* * * * *